United States Patent
Noda et al.

(10) Patent No.: US 10,881,536 B2
(45) Date of Patent: Jan. 5, 2021

(54) ACTUATOR DEVICE, POWER ASSIST ROBOT AND HUMANOID ROBOT

(71) Applicant: ADVANCED TELECOMMUNICATIONS RESEARCH INSTITUTE INTERNATIONAL, Kyoto (JP)

(72) Inventors: Tomoyuki Noda, Soraku-gun (JP); Jun Morimoto, Soraku-gun (JP)

(73) Assignee: ADVANCED TELECOMMUNICATIONS RESEARCH INSTITUTE INTERNATIONAL, Kyoto (JP)

( * ) Notice: Subject to any disclaimer, the term of this patent is extended or adjusted under 35 U.S.C. 154(b) by 491 days.

(21) Appl. No.: 15/501,646

(22) PCT Filed: Aug. 26, 2015

(86) PCT No.: PCT/JP2015/073978
§ 371 (c)(1),
(2) Date: Feb. 3, 2017

(87) PCT Pub. No.: WO2016/039140
PCT Pub. Date: Mar. 17, 2016

(65) Prior Publication Data
US 2017/0231787 A1    Aug. 17, 2017

(30) Foreign Application Priority Data

Sep. 12, 2014 (JP) .................... 2014-186931

(51) Int. Cl.
*A61F 2/70* (2006.01)
*A61H 3/00* (2006.01)
(Continued)

(52) U.S. Cl.
CPC .............. *A61F 2/70* (2013.01); *A61F 2/68* (2013.01); *A61H 1/00* (2013.01); *A61H 3/00* (2013.01);
(Continued)

(58) Field of Classification Search
CPC ................ A61F 2/68; A61F 2002/74; A61F 2005/0016; A61F 2250/0001; A61F 5/003;
(Continued)

(56) References Cited

U.S. PATENT DOCUMENTS 5,031,510 A    7/1991   Krauter
6,223,648 B1 * 5/2001  Erickson ............... F15B 15/103
                                                    92/92
(Continued)

FOREIGN PATENT DOCUMENTS

JP    60-234105 A    11/1985
JP    2-125102 A     5/1990
(Continued)

OTHER PUBLICATIONS

Au et al. "An Ankle-Foot Emulation System for the Study of Human Walking Biomechanics", Proceedings of the 2006 IEEE International Conference on Robotics and Automation, Orlando, Florida—May 2006, pp. 2939-2945.
(Continued)

*Primary Examiner* — Ann Schillinger
(74) *Attorney, Agent, or Firm* — Birch, Stewart, Kolasch & Birch, LLP

(57) ABSTRACT

[Object] To provide a hybrid actuator attaining both driving force and responsiveness, capable of reducing inertia of a movable portion.
[Solution] A pneumatic air muscle has a cylinder (112) provided in a flexible member (100) forming a pneumatic
(Continued)

artificial muscle. At the center of an upper lid element (109) of the cylinder, a through hole is opened, and an inner wire (103) of a Bowden cable passes through this through hole and is coupled by means of a spring (106) to a bottom portion of the cylinder. When the pneumatic artificial muscle contracts, the inner wire (103) and the pneumatic air muscle move together because of the stopper (105), and the contraction force is transmitted. In contrast, when the pneumatic air muscle extends, the stopper (105) is disengaged, while the tension of inner wire (103) is kept by the spring (106) to prevent slacking.

8 Claims, 13 Drawing Sheets

(51) Int. Cl.
| | |
|---|---|
| *F15B 15/08* | (2006.01) |
| *B25J 9/00* | (2006.01) |
| *B25J 9/14* | (2006.01) |
| *B25J 13/08* | (2006.01) |
| *B25J 9/10* | (2006.01) |
| *A61F 2/68* | (2006.01) |
| *A61H 1/00* | (2006.01) |
| *F15B 15/10* | (2006.01) |
| *F16C 1/12* | (2006.01) |
| *F15B 15/06* | (2006.01) |
| *F15B 15/14* | (2006.01) |
| *A61F 2/74* | (2006.01) |

(52) U.S. Cl.
CPC ............. *B25J 9/0006* (2013.01); *B25J 9/104* (2013.01); *B25J 9/1045* (2013.01); *B25J 9/1075* (2013.01); *B25J 9/14* (2013.01); *B25J 9/142* (2013.01); *B25J 9/144* (2013.01); *B25J 13/085* (2013.01); *B25J 13/087* (2013.01); *F15B 15/103* (2013.01); *F16C 1/12* (2013.01); *A61F 2002/74* (2013.01); *F15B 15/06* (2013.01); *F15B 15/1404* (2013.01); *Y10S 901/21* (2013.01); *Y10S 901/22* (2013.01)

(58) Field of Classification Search
CPC ............ A61F 5/0033; A61F 2002/0894; A61F 2002/5012; A61F 2002/5036; A61F 2002/5066; A61F 2002/747; A61F 2005/0188; A61H 2201/165; A61H 9/0078; A61H 2201/10; A61H 3/00; A61H 2201/5061; A61H 2230/305; A61H 2230/405; A61H 2230/625; A61H 2201/1676; A61H 2205/06; A61H 2205/10; A61H 2205/106; A61H 2205/108; A61H 15/0078; A61H 2015/0014; A61H 2201/0103; A61H 2201/0165; A61H 2201/5056
See application file for complete search history.

(56) References Cited

U.S. PATENT DOCUMENTS

| | | | |
|---|---|---|---|
| 8,573,534 B2 * | 11/2013 | Kothera | ............... B64C 27/72 244/99.2 |
| 2008/0035798 A1 * | 2/2008 | Kothera | ............... B63B 1/248 244/212 |

FOREIGN PATENT DOCUMENTS

| | | | |
|---|---|---|---|
| JP | 4-170931 | A | 6/1992 |
| JP | 2007-32743 | A | 2/2007 |
| JP | 2012-45194 | A | 3/2012 |
| JP | 2014-57626 | A | 4/2014 |
| JP | 2014-104549 | A | 6/2014 |
| JP | 2014-155998 | A | 8/2014 |
| WO | WO 2007/139135 | A1 | 12/2007 |

OTHER PUBLICATIONS

Caldwell et al. "Braided Pneumatic Muscle Actuators", in Proceedings of the IFAC Conference on Intelligent Autonomous Vehicles, 1993, pp. 507-512.
Carlson et al. "Efficiency of Prosthetic Cable and Housing", JPO: Journal of Prosthetics and Orthotics, vol. 7, No. 3, pp. 96, 1995.
Hildebrandt et al. "Cascaded control concept of a robot with two degrees of freedom driven by four artificial pneumatic muscle actuators", 2005, American Control Conference, Jun. 8-10, 2005, Portland, OR, USA, pp. 680-685.
Kagawa et al. "Gait pattern generation for a power-assist device of paraplegic gait", The 18th IEEE International Symposium on Robot and Human Interactive Communication, Toyama, Japan, Sep. 27-Oct. 2, 2009, pp. 633-638.
Kanji Inoue, "Rubbertuators and Applications for Robots", in Proceedings of the 4th international symposium on Robotics Research, MIT press, 1988, pp. 57-63.
Kobayashi et al. "Muscle Suit Development and Factory Application", International Journal of Automation Technology, vol. 3, No. 6, pp. 709-715, 2009.
Noda et al. "Brain-Controlled Exoskeleton Robot for BMI Rehabilitation", Proceedings of IEEE-RAS International Conference on Humanoids (Humanoids), 2012.
Suzuki et al. "Intention-based walking support for paraplegia patients with Robot Suit HAL", Advanced Robotics, vol. 21, No. 12, pp. 1441-1469, (2007).
Toyama et al. "Development of Wearable-Agri-Robot Mechanism for Agricultural Work", The 2009 IEEE/RSJ International Conference on Intelligent Robots and Systems, Oct. 11-15, 2009, St. Louis, USA, pp. 5801-5806.

\* cited by examiner (a)

(b)

ACTUATOR DEVICE, POWER ASSIST ROBOT AND HUMANOID ROBOT

TECHNICAL FIELD

The present invention relates to a technique of actuator devices and, more specifically, to a power assist robot and a humanoid robot supporting movement of a user, by using an actuator device.

BACKGROUND ART

There is an increasing demand for assist devices applying robotics techniques in many countries, including Japan, facing the concerns of fewer children and aging population. In the meantime, robots capable of maintaining balance or walking have been developed. By way of example, there is a robot capable of generating torques at various joints like a human being, by optimally distributing acting force necessary for movement to a plurality of any given contact points in a space (see Patent Literature Document 1).

Recently, development of robots assisting rehabilitation, such as exoskeleton robots aimed to assist lower limb/trunk movement has been strongly desired. An exoskeleton robot, for example, is used in rehabilitation of a patient suffering from spinal damage to promote self-reliant living (see Patent Literature Documents 1, 2, 3, 4 and 5).

An exoskeleton robot can be used for assisting action of an elderly, and the exoskeleton robot can be a useful device assisting recovery of a patient of cerebral stroke or spinal cord injury, who needs rehabilitation.

An arm of an exoskeleton robot must have small inertia for the reasons of agility and safety; therefore use of a heavy actuator is undesirable. By contrast, it is necessary to use an actuator that can generate torque large enough to assist actions of a user. There seems to be a trade-off between these two requirements.

In order to solve this problem encountered in developing exoskeleton robots, techniques using hybrid operation systems consisting of PAM (Pneumatic Artificial Muscles) and a small-sized motor have been reported (see Patent Literature Documents 2, 3, 4 and 5).

CITATION LIST

Patent Literature Documents

PTL 1: WO2007/139135
PTL 2: JP2012-045194 A
PTL 3: JP2014-57626 A
PTL 4: JP2014-104549 A
PTL 5: JP2014-155998 A

Non Patent Literature Documents

NPL 1: K. Suzuki, G. Mito, H. Kawamoto, H. Hasegawa, and Y. Sankai, "Intention-based walking support for paraplegia patients with Robot Suit HAL," Advanced Robotics, vol. 21, no. 12, pp. 1441-1469, 2007.
NPL 2: S. K. Au, P. Dilworth, and H. Herr. An ankle-foot emulation system for the study of human walking biomechanics. In IEEE International Conference on Robotics and Automation, pp. 2939-2945, 2006.
NPL 3: H. Kobayashi, T. Aida, and T. Hashimoto. Muscle Suit Development and Factory Application. International Journal of Automation Technology, Vol. 3, No. 6, pp. 709-715, 2009.
NPL 4: G. Yamamoto and S. Toyama. Development of Wearable Agri-Robot-Mechanism for Agricultural Work. In IEEE/RSJ International Conference on Intelligent Robots and System, pp. 5801-5806, 2009.
NPL 5: T. Kagawa and Y. Uno. Gait pattern generation for a power-assist device of paraplegic gait. In The 18th IEEE International Symposium on Robot and Human Interactive Communication, pp. 633-638, 2009.

SUMMARY OF INVENTION

Technical Problem

Considering the situation of assisting human actions using a hybrid-type actuator, it is desirable that joints and actuator portions of an exoskeleton robot have even smaller inertia and have back-drivability. Particularly when assisting actions of upper limbs of a human, the inertia should desirably be smaller than when assisting lower limbs.

Further, when such a hybrid-type actuator is applied to a humanoid robot, movable parts thereof should desirably be of small weight.

The present invention was made to solve the above-described problems, and its object is to provide a hybrid-type actuator device realizing both driving force and responsiveness, in which inertia of movable parts can be reduced.

Another object of the present invention is to provide a power assist robot and a humanoid robot using the hybrid-type actuator realizing both driving force and responsiveness and having movable parts with reduced inertia.

Solution to Problem

According to an aspect, the present invention provides an actuator device driven by fluid pressure, including: a fluid pressure artificial muscle having one end fixed and contracting in a longitudinal direction with increase of the fluid pressure introduced from outside to a fluid bladder for driving; a flexible driving force transmitting cable for transmitting contraction force of the fluid pressure artificial muscle from the other end of the fluid pressure artificial muscle to an object to be driven; a stopper fixed at a prescribed position of the driving force transmitting cable; an engaging member provided on a side of the other end of the fluid pressure artificial muscle for transmitting the contraction force of the fluid pressure artificial muscle to the driving force transmitting cable by engaging with the stopper in response to contraction of the fluid pressure artificial muscle being a prescribed amount or larger; and energizing means for applying, when the stopper and the engaging member are not in the engaged state, tensile force to the driving force transmitting cable to maintain tension.

Preferably, the actuator device further includes a cylinder provided in the fluid pressure artificial muscle fixed to the other end of the fluid pressure artificial muscle and having the inside sealed from the fluid pressure. The engaging member is a lid of the cylinder provided at the other end of the fluid pressure artificial muscle. The lid has a through hole through which the driving force transmitting cable passes. The stopper is fixed to the driving force transmitting cable inside the cylinder, has an outer diameter not smaller than the through hole and is engageable with the through hole. The energizing means is a resilient member coupling the stopper with a bottom portion of the cylinder.

Preferably, the driving force transmitting cable is a Bowden cable.

Preferably, the fluid pressure artificial muscle has both ends fixed inside a frame structure. The driving force transmitting cable is coupled with the object to be driven through a through hole at one end side of the frame structure.

Preferably, a force sensor for detecting contraction force of the fluid pressure artificial muscle is provided between an inner surface of the other end side of the inside of the frame structure and the fluid pressure artificial muscle.

Preferably the object to be driven is a joint structure body, and the actuator device further includes: a pulley provided at a movable portion of the joint, receiving first torque by the contraction force transmitted by the driving force transmitting cable; and an electric motor coupled to the pulley, for applying second torque to the pulley.

According to another aspect, the present invention provides a power assist robot assisting musculoskeletal movement of a user, including: a frame structure corresponding to an exoskeleton; an active joint arranged for applying a support force to a joint of the user as an object in the musculoskeletal movement; and an actuator device driving the active joint. The actuator device includes: a fluid pressure artificial muscle having one end fixed and contracting in a longitudinal direction with increase of the fluid pressure introduced from outside to a fluid bladder for driving; a flexible driving force transmitting cable for transmitting contraction force of the fluid pressure artificial muscle from the other end of the fluid pressure artificial muscle to an object to be driven; a stopper fixed at a prescribed position of the driving force transmitting cable; an engaging member provided on a side of the other end of the fluid pressure artificial muscle for transmitting the contraction force of the fluid pressure artificial muscle to the driving force transmitting cable by engaging with the stopper in response to contraction of the fluid pressure artificial muscle being a prescribed amount or larger; and energizing means for applying, when the stopper and the engaging member are not in the engaged state, tensile force to the driving force transmitting cable to maintain tension. The power assist robot further includes a control unit for operating the active joint by controlling torque to the active joint.

According to a still further aspect, the present invention provides a humanoid robot, including: a frame structure corresponding to a human skeleton; an active joint arranged to apply a driving force to a joint of the frame structure; and an actuator device driving the active joint. The actuator device includes: a fluid pressure artificial muscle having one end fixed and contracting in a longitudinal direction as the fluid pressure introduced from outside to a fluid bladder for driving increases; a flexible driving force transmitting cable for transmitting contraction force of the fluid pressure artificial muscle from the other end of the fluid pressure artificial muscle to an object to be driven; a stopper fixed at a prescribed position of the driving force transmitting cable; an engaging member provided on a side of the other end of the fluid pressure artificial muscle for transmitting the contraction force of the fluid pressure artificial muscle to the driving force transmitting cable by engaging with the stopper in response to contraction of the fluid pressure artificial muscle being a prescribed amount or larger; and energizing means for applying, when the stopper and the engaging member are not in the engaged state, tensile force to the driving force transmitting cable to maintain tension.

Advantageous Effects of Invention

According to one aspect of the present invention, it is possible to reduce inertia of movable parts while realizing both driving force and responsiveness.

DESCRIPTION OF EMBODIMENTS

Figure 1:
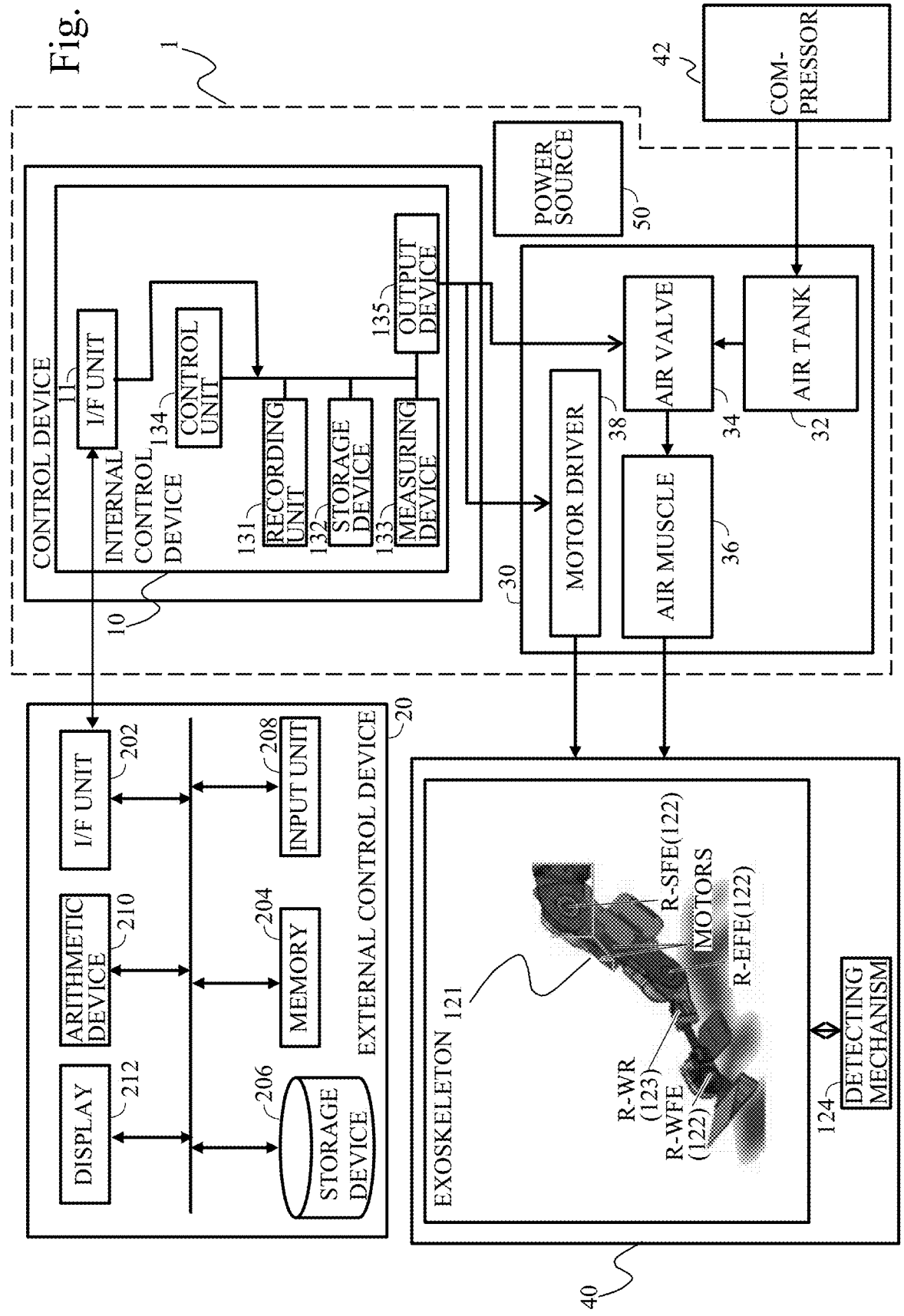
FIG. 1 is an example of a block diagram showing an exoskeleton robot for upper limbs.

In the following, structures of exoskeleton robots in accordance with embodiments of the present invention will be described with reference to the drawings. In the embodiments described below, the components and process steps denoted by the same reference characters are the same or corresponding components or steps; therefore, description thereof will not be repeated unless necessary.

Further, as an example of an actuator for driving a joint of an exoskeleton robot, a "pneumatic-electric hybrid actuator" as will be described below is used.

In the following embodiments, an exoskeleton robot using a pneumatic-electric hybrid actuator for rehabilitation of upper limbs will be described.

It is noted, however, that the pneumatic-electric hybrid exoskeleton robot in accordance with the present invention can be used not only for the exoskeleton robot for assisting movements of upper limbs but also for exoskeleton robots for assisting movements of lower limbs.

Though an exoskeleton robot assisting movements of upper limbs as a pair will be described below, it may also be used as an exoskeleton robot for assisting movements of either one of the upper limbs, or either one of the lower limbs.

Further, the hybrid exoskeleton robot of the present invention is not limited to assisting movements of at least "one of the upper limbs, or one of the lower limbs" as described above, and it may assist any musculoskeletal movement of a human as an object. For instance, it may assist only the movement of hips of the human as an object, or it may assist the movement of hips in connection with the movement of lower limbs when one is walking or running. In the present specification, assists for the human movements as the object will be generally referred to as "assist of musculoskeletal movements of a human as an object."

The exoskeleton robot in accordance with an embodiment has an exoskeleton. The "exoskeleton" means a skeletal structure of the robot that corresponds to the skeletal structure of a human. Specifically, the "exoskeleton" refers to a frame structure (framework) supporting from outside part of the body of the human who wears the exoskeleton robot.

The frame structure is further provided with joints for moving each part of the frame structure in accordance with movements based on the human skeletal structure.

Specifically, the exoskeleton robot assisting movements of upper limbs has shoulder portions, elbow portions, and wrist portions, and has joints at least at positions corresponding to the shoulders, the elbows and left and right sides of the wrists. The joints are pneumatic-electric hybrid-driven. In the following, a joint driven by an actuator for exerting support force for a joint of the user in the exoskeleton robot will be referred to as an "active joint." A joint that moves in a passive manner as the user moves will be referred to as a "passive joint."

First Embodiment

FIG. 1 is an example of a block diagram showing an exoskeleton robot for upper limbs.

A command for controlling an exoskeleton robot 40 is given from an external control device 20 through a communication path to the exoskeleton robot. Though not specifically limited, a general personal computer may be used as external control device 20, and Ethernet (registered trademark) cable may be used as the communication path. It goes without saying that wired communication paths of other standards as well as wireless communication path such as wireless LAN (Local Area Network), or wireless communication of other standard may be used as the communication path.

External control device 20 includes: an input unit 208 receiving an instruction input from a user; a non-volatile storage device 206 recording a program or programs for generating commands as well as data necessary for control such as various control parameters; a memory 204 including an ROM (Read Only Memory) storing a firm wear for activating external control device 20 and an RAM (Random Access Memory) operating as a working memory; an arithmetic device 210 executing the process of generating commands in accordance with a program; an interface (I/F) unit 202 for transmitting the commands through the communication path to the exoskeleton robot; and a display 212 for displaying, for example, information related to the state of control of exoskeleton robot 40 under the control of arithmetic device 210.

As described above, when a general personal computer is used as external control device 20, arithmetic device 210 is implemented by a CPU (Central Processing Unit), and a hard disk drive or a solid state drive may be used as non-volatile storage device 206. It is noted, however, that part or all of the functional blocks of external control device 20 may be realized by dedicated hardware.

Further, external control device 20 performs a process of configuring, at the time of calibration, a model for estimating joint torque from detected joint angle and contraction force of a user who wears the exoskeleton robot.

The exoskeleton robot further includes an exoskeleton 121 and an internal control device 10. The figure only shows an exoskeleton 121 of the right arm.

Exoskeleton 121 includes frames corresponding to the upper arm, the forearm and the palm, respectively, and an active joint 122, a passive joint 123 and a detecting mechanism 124. Further, active joint 122 includes a shoulder joint R-SFE, an elbow joint R-EFE, and a wrist joint R-WFE. As will be described later, the active joint includes a pulley (not shown) driven by a contraction force transmitted by a driving force transmitting cable from an air muscle (not shown), and an electric motor (not shown) for driving the pulley. On the forearm, a passive joint R-WR is provided.

Specifically, active joint 122 is a hybrid actuator receiving driving forces both from the air muscle and the electric motor. The actuator has a function of receiving, as a driving signal, a torque value as a control target value and performing control based on the received torque value. If a servo motor is used as the actuator, a servo motor having a driving circuit allowing current control and generating torque in proportion to the current is used as the actuator. The servo motor realizes such torque control that the torque value input as the control target value is multiplied by a torque constant determined by gear ratio, and the result is given as an instruction to the driving circuit, so that the input torque is generated. Particularly, a torque sensor is arranged at active joint 122 and the value detected by the torque sensor is fedback to the driving circuit, so that highly accurate torque control is possible.

The detecting mechanism 124 detects joint angle of each joint and torque of each joint. By way of example, detecting mechanism 124 is an angle sensor for detecting joint angle arranged at each joint, or a load cell for detecting driving force of each air muscle.

Internal control device 10 includes an I/F unit 11, a recording unit 131, a storage device 132, a measuring device 133, a control unit 134 and an output device 135.

I/F unit 11 can receive instructed torque or a position instruction from external control device 20.

Internal control device 10 operates active joint 122. Internal control device 10 operates active joint 122 in response to target torque or a position instruction received by I/F unit 11.

Measuring device 133 receives various signals (data) representing results of detection from detecting mechanism 124 such as a sensor. Control unit 134 performs various arithmetic operations such as calculation of control target value.

Output device 135 outputs a control signal to driving unit 30. By way of example, output device 135 drives air muscle 36 by outputting a target air muscle pressure value to air valve 34, or outputs a motor control value to motor driver 38. Compressed air compressed by compressor 42 and stored in air tank 32 is supplied to air muscle 36 through air valve 34, and the contraction force of air muscle 36 is transmitted as a driving force by the driving force transmitting cable to the active joint. The motor at the active joint portion is driven by motor driver 38.

Power source 50 supplies electric power to internal control device 10 and driving unit 30.

Driving unit 30 and power source 50 may be fixed on the ground, or if the subject is on a wheel chair, these may be mounted on a rear portion or the like of the wheel chair.

Further, as the "driving force transmitting cable," a Bowden cable, which is used, for example, for a braking mechanism of a bicycle, consisting of a hollow outer case and a metal wire passed therethrough, flexible and capable of transmitting force, may be used. In the following description, it is assumed that the driving force transmitting cable is a Bowden cable.

Internal control device 10, driving unit 30 and power source 50 may be an integrated controller unit 1, which may be mounted, for example, on a rear portion or the like of a wheel chair as described above.

The above-described air muscle is light. Nevertheless, the pneumatic air muscle can generate a large force as it converts energy of the compressed air (or compressed gas: hereinafter generally referred to as "compressed fluid") to a contraction force by means of a rubber tube.

The principle of air muscle generating force is that spiral fiber having pneumatic bladder embedded therein contracts in the lengthwise direction (longitudinal direction) of the bladder when compressed air is fed to the bladder and the bladder expands.

More specifically, the air muscle has such a structure that a rubber tube closed at both ends by plugs has its surface covered by spiral fibers, so that the radial direction of the tube is constrained. When air is fed to the tube, the rubber tube expands by the air pressure. The tube, however, cannot expand in the radial direction as it is restrained by the fibers; therefore, the tube contracts in the longitudinal direction as it is being pulled by the expansion in the radial direction. The manner of simultaneous expansion and contraction is similar to movements of an animal muscle and, hence, this structure is referred to as an artificial muscle.

The actuator itself is light and flexible. Further, the inner surface of the rubber tube as a whole contributes to contraction of the actuator. Therefore, as compared with a general cylinder or the like which is so structured as to receive pressure only by the cross-section, larger power-weight ratio can be attained. On the other hand, generally, apparatus control using air pressure has a long lag inherent to air contraction/expansion and hence it is not very suitable for quick operation, as described above.

The "pneumatic bladder" may be any bag that can be expanded/contracted by fluid, and the fluid to be fed to the bag is not limited to air. Therefore, the pneumatic bladder may more generally be referred to as a "fluid bladder."

Therefore, here, a pneumatic air muscle is also referred to as "pneumatic artificial muscle" and more generally, to include fluid other than the air, it is referred to as "fluid pressure artificial muscle."

In the following, however, a pneumatic air muscle will be described as a specific example.

Figure 2:
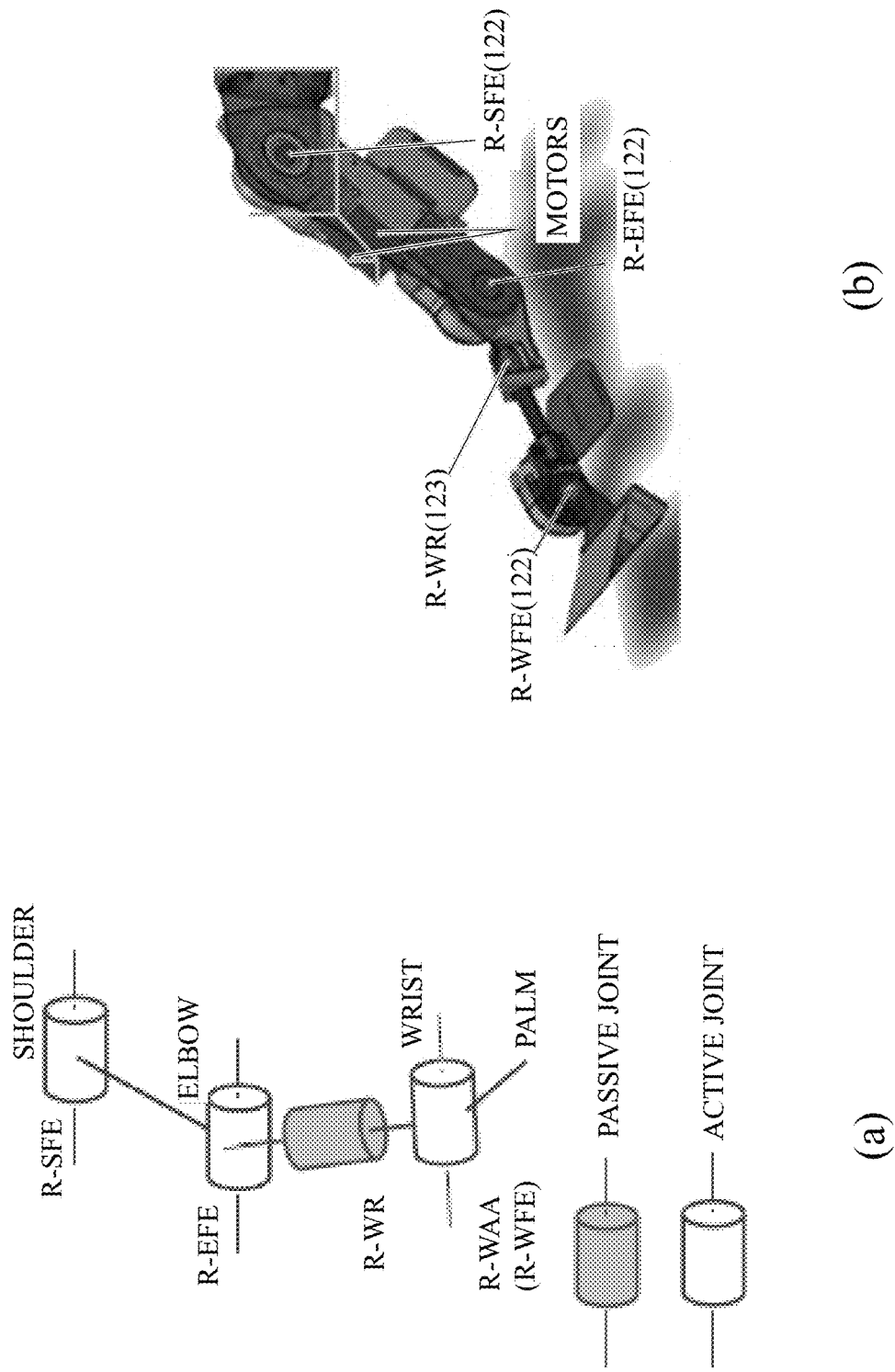
FIG. 2 shows a kinematic structure of an exoskeleton for an upper right arm.

FIG. 2 shows a kinematic structure of an exoskeleton for an upper right arm.

As shown at (a) of FIG. 2, to a joint portion of an exoskeleton, driving force is supplied by a pneumatic-electric hybrid actuator provided with a Bowden cable. At the shoulder portion, the elbow portion and the wrist portion, active flexion-extension (FE: flexion-extension) joints SFE, EFE and WAA are provided. Therefore, at each joint SFE, EFE, and WAA, a pulley is provided at the joint portion, and driving force from the pneumatic air muscle is transmitted through the Bowden cable and hence torque is applied to the pulley. In addition, at the pulley portion, an electric motor is also provided and torque is also applied to the pulley by the electric motor.

It is noted, however, that the electric motor is not provided on the wrist portion in order to reduce weight, and only the driving force generated by a set of antagonistic pneumatic air muscles is supplied to the flexion-extension joint WFE at the wrist.

Further, on the forearm portion, a passive joint WR is provided to cope with the twisting motion of one's arm.

Here, the letter "R-" represents that the corresponding joint is for the right arm. The letter "L-" is added if it is for the left arm.

In FIG. 2, (b) shows an appearance of an exoskeleton arm by 3D CAD assembly.

By way of example, assuming a task holding a typical user's arm itself and a weight of 5 kg for each hand with each joint angle being (θSFE, θEFE)=(0, 0) or a weight of 10 kg with (θSFE, θEFE)=(−π/2, 0), the diameter of the pneumatic air muscle and the radius of the pulley can be selected.

The torque from the motor is transmitted by a reduction gear (14:1) and a bevel gear (2:5). The joint angle is measured by an optical quadrature phase encoder.

Because of the reduction gear, the joint is back-drivable by a small force. The motor torque, however, is not sufficient to hold the user's arm in anyway. On the other hand, the torque from the pneumatic air muscle has a slow response. Therefore, a structure combining the torque by the pneumatic air muscle and the motor torque to compensate for each other is reasonable to hold a man's arm.

[Pneumatic-Electric Hybrid Actuator with One Degree of Freedom]

In the following, in order to demonstrate the structure and operation of pneumatic-electric hybrid actuator in accordance with the present embodiment, a pneumatic-electric hybrid actuator with one degree of freedom will be described as an example.

Figure 3:
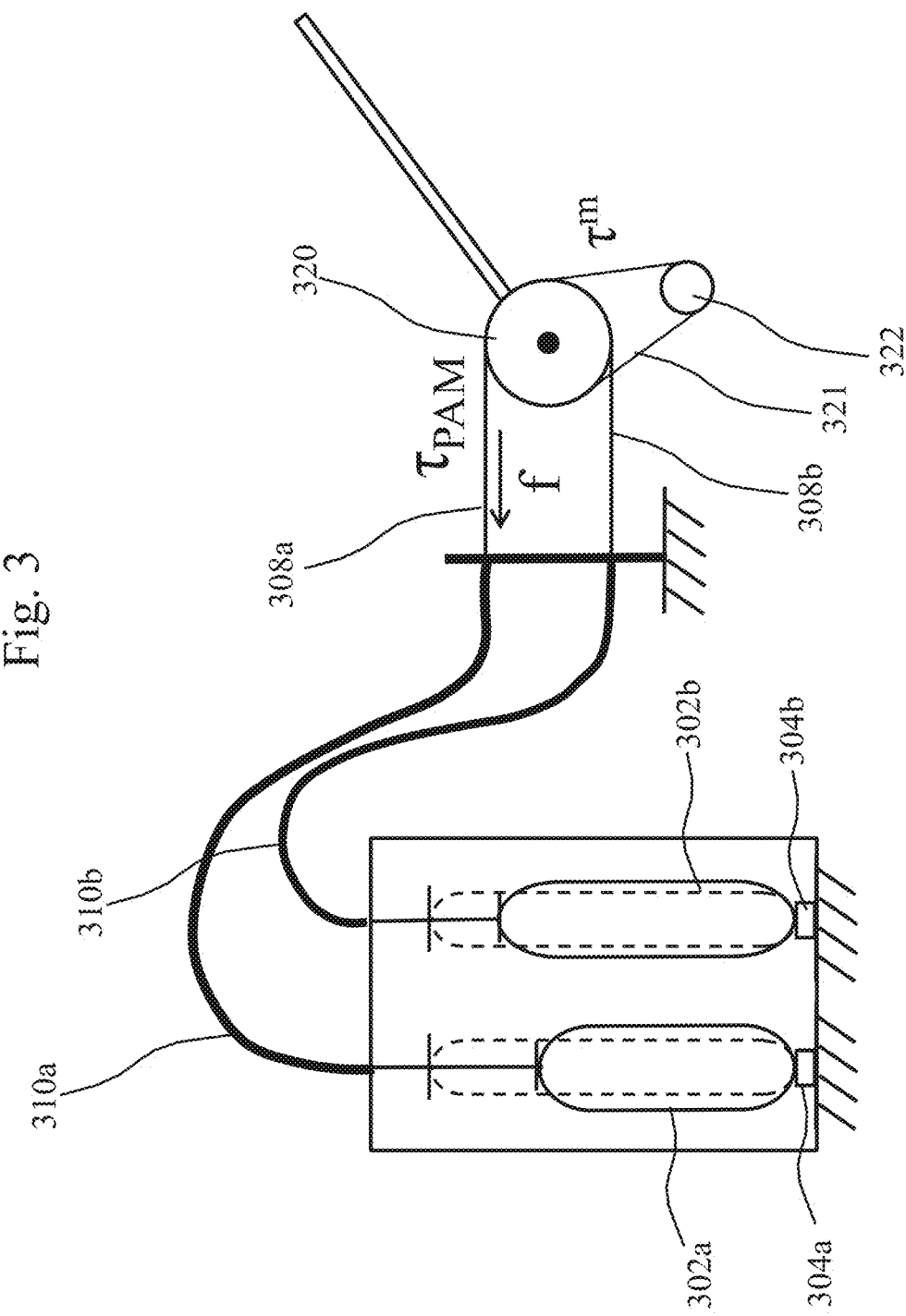
FIG. 3 shows a structure of a pneumatic-electric hybrid actuator system of one degree of freedom in accordance with First Embodiment.

FIG. 3 shows a structure of a pneumatic-electric hybrid actuator system of one degree of freedom (PEHA 1-DOF) in accordance with First Embodiment.

Two antagonizing pneumatic air muscles 302a and 302b generate opposing contraction forces, which are transmitted by inner wires 308a and 308b in Bowden cables 310a and 310b to pulley 320, respectively.

The torque of motor 322 is transmitted by a transmission mechanism 321 such as a belt or a gear, to pulley 320.

A Bowden cable consists of an inner wire and a flexible outer case. By using a Bowden cable for transmitting force, it becomes possible to reduce weight of exoskeleton robot 40 worn by a human and to save structural space of the robot frame.

The sum τ of torque at pulley 320 is the sum of the torque by the pneumatic air muscle ($\tau_{PAMs}$) and the torque of motor 312 ($\tau_{motor}$).

$$\tau = \tau_{PAMs} + T_{motor} = (f_{PAM1} - f_{PAM2})r_0 + \tau_{motor} \quad \text{(Equation 1)}$$

Here, $f_{PAM1}$ is the contraction force of pneumatic air muscle 302a, and $f_{PAM2}$ is the contraction force of pneumatic air muscle 302b. Further, $r_0$ represents pulley radius. An elliptical pulley may be used as well as a circular pulley.

Since the torque of electric motor 322 and the time responsiveness of pneumatic air muscle 302 (generally referring to pneumatic air muscles 302a and 302b) have such characteristics as described above, the pneumatic air muscle covers large torque for generating low frequency torque or for gravity compensation. Though motor 322 covers high-frequency torque, the torque is made small by a reduction gear with low gear ratio for back-drivability.

Between the bottom of an external frame containing the pneumatic air muscles and the lower ends of pneumatic air muscles 302a and 302b, load cells 304a and 304b are provided for detecting contraction forces of pneumatic air muscles, respectively.

Figure 4:
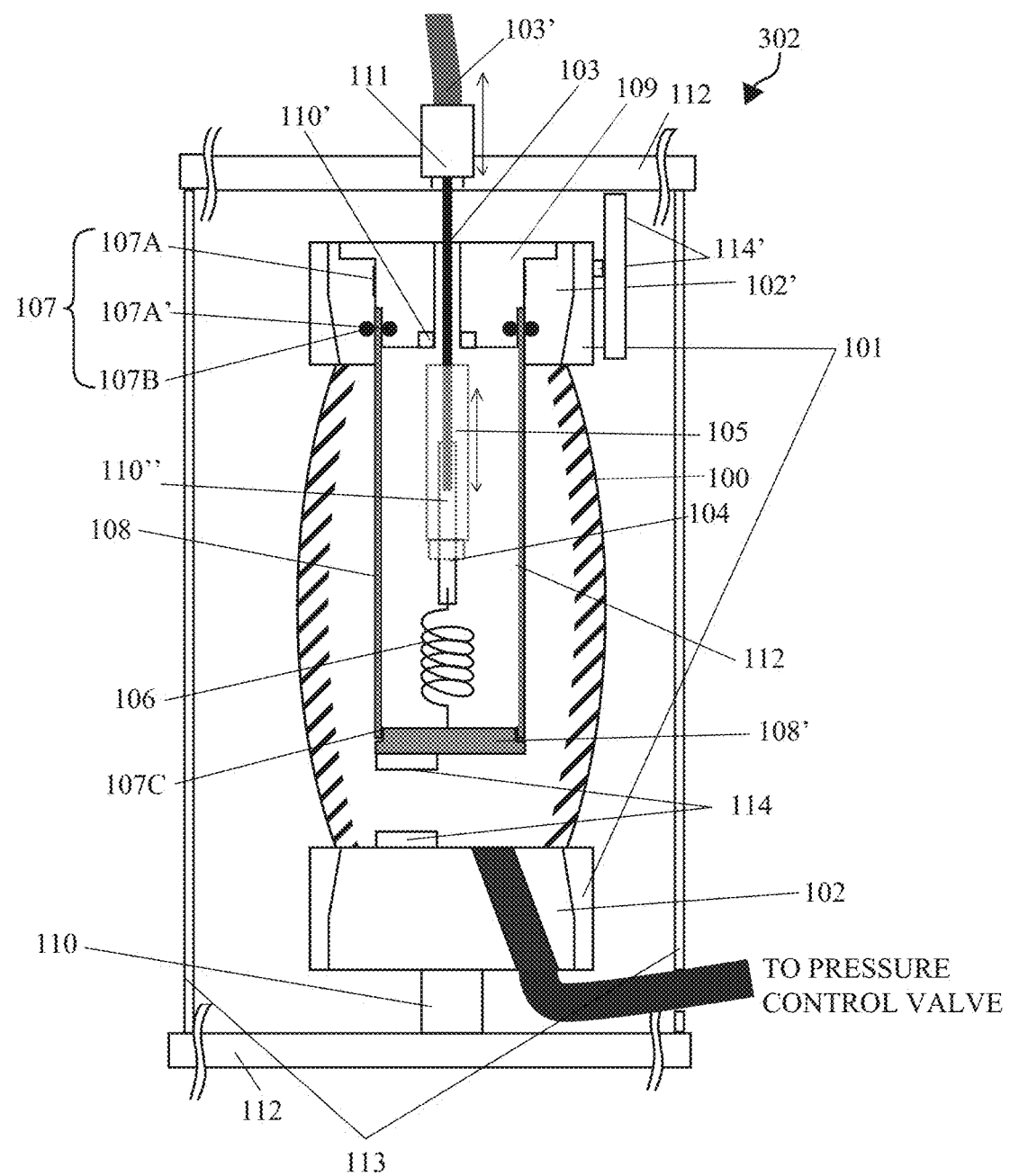
FIG. 4 is a cross-sectional view showing a structure of a pneumatic air muscle.

FIG. 4 is a cross-sectional view showing a structure of a pneumatic air muscle shown in FIG. 3.

Referring to FIG. 4, pneumatic air muscle 302 includes a flexible material 100 forming a chamber of an artificial muscle. The inside of flexible material 100 is filled with compressed air (surrounding regions are hatched), so that the pressure is converted to tension inside the artificial muscle portion. The flexible material 100 means the above-described integrated material of spiral fiber having pneumatic bladder embedded.

The flexible material 100 is held by friction between an element 101 holding the outer side of an end portion of flexible material 100 and an element 102 coupled with an end portion of pneumatic air muscle 302, and maintains seal from the atmospheric pressure.

The element 102 holding inside of one end of flexible material 100 has an air supply inlet connected to a pressure control valve. While an element 102' holding inside of the other end of flexible material 100 has the same function of holding the inside of the end portion of flexible material 100 as that of element 102, it has an inner screw at its center, for connecting to an element 109.

The Bowden cable consists of an inner wire 103 and an outer coat member 103'.

An element 104 is connected to an end of inner wire 103 and can be passed through a through hole of element 109. Element 104 and the end of inner wire 103 may be joined, for example, by swaging, and a screw is formed at a lower portion of element 104.

An element 105 is a cylindrical member having a thread formed inside, and engaged with a thread groove formed on the outer circumference of element 104 to cover the outside of element 104. By changing the amount of screw-in, the attachment position of element 105 can be adjusted in the up/down direction. Element 105 is larger than the through hole of element 109; therefore, after the upper end of element 105 contacts the lower end of element 109 when pneumatic air muscle 302 contracts, element 109 and element 102' move together with inner wire 103, and the contracting force of flexible material 100 is transmitted to wire 103. Then, element 105 functions as a stopper for transmitting the contraction force of pneumatic air muscle 302 to wire 103.

A resilient member 106 is a member for pulling down element 104 and, by way of example, a spring may be used. When element 105 moves away from the upper end, spring 106 provides certain tension to wire 103, so as to prevent slacking of wire 103.

A member 107 is a seal member separating the atmosphere from the compressed air (gray) in the artificial muscle chamber. For instance, the upper end of member 107 may be a combination of seal members 107A and 107A', or an O-ring 107B may be used to seal between the atmosphere pressure inside a pipe cylinder 108 and the air pressure in the artificial muscle chamber. Further, the lower end of pipe cylinder 108 is sealed by a bottom lid 108' and a seal member 107c (or an O-ring).

Pipe cylinder 108 has an outer diameter smaller than the inner diameter of the screw of element 102'.

Element 109 also functions as an upper lid of pipe cylinder 108, and it has such a structure that can be screwed in the thread groove inside the element 102'. Further, the outer diameter at the tip end of element 109 is smaller than the inner diameter of pipe cylinder 108, and when screwed in, the tip end enters the inside of pipe cylinder 108, and tight-seal is kept by the seal member 107, as described above.

A force sensor 110 measures tension of the artificial muscle, and a load cell, for example, may be used. In order to measure the tension of the artificial muscle, a hollow load cell 110' may be arranged at the center of element 109.

An element 111 is for holding outer coat member 103' of the Bowden cable.

Pneumatic air muscle 302 is contained in a frame, and the frame consists of upper and lower plates 112 and pillars 113 formed of wire. The frame serves to keep constant the distance between the end portion of actuator and element 111.

The structure shown in FIG. 4 allows measurement of contraction rate of the artificial muscle and allows force control. By way of example, by providing a laser distance meter 114 and an optical encoder at the lower surface of bottom lid 108' and the upper surface of element 102, the contraction rate of pneumatic air muscle 302 can directly be measured, and using this, force control is possible. It is noted that the contraction rate can also be measured by using an encoder attached, for example, to the opposite tip end (driving joint portion) of pillar 113.

It is possible to use a pipe as a substitute for pillar 113. In that case, a pressure-tension converting module not exposing any of the artificial muscle, the sensors and the movable parts can be realized.

Figure 5:
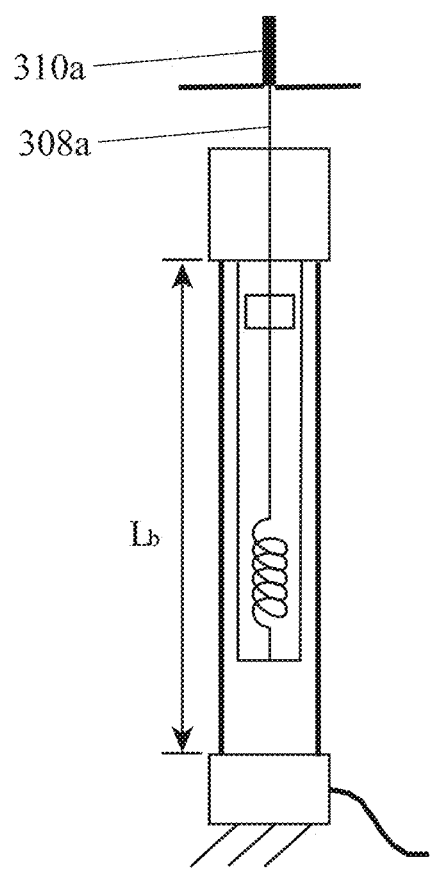
FIG. 5 schematically illustrates extended and contracted states of a pneumatic air muscle 302.
Figure 5:
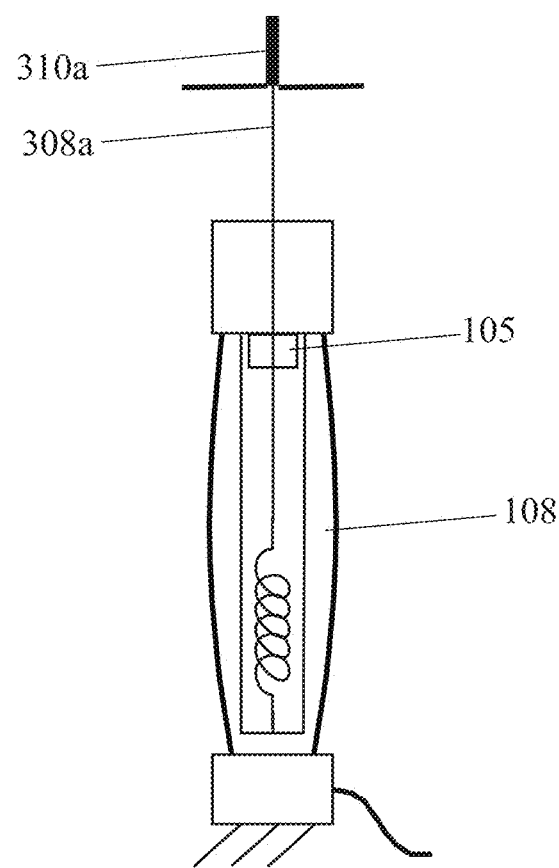

FIG. 5 schematically illustrates extended and contracted states of pneumatic air muscle 302 shown in FIG. 4.

As described above, at a portion where the upper end of element 105 (stopper) abuts the lower end of element 109 when pneumatic air muscle 302 contracts, inner wire 103 is integrated with element 109 and element 102', and the contracting force of flexible material 100 is transmitted to wire 103.

On the other hand, spring 106 is a member for pulling the element 104 downward and, when element 105 moves away from the upper end, spring 106 applies certain tension to wire 103, to prevent slacking of wire 103.

Figure 6:
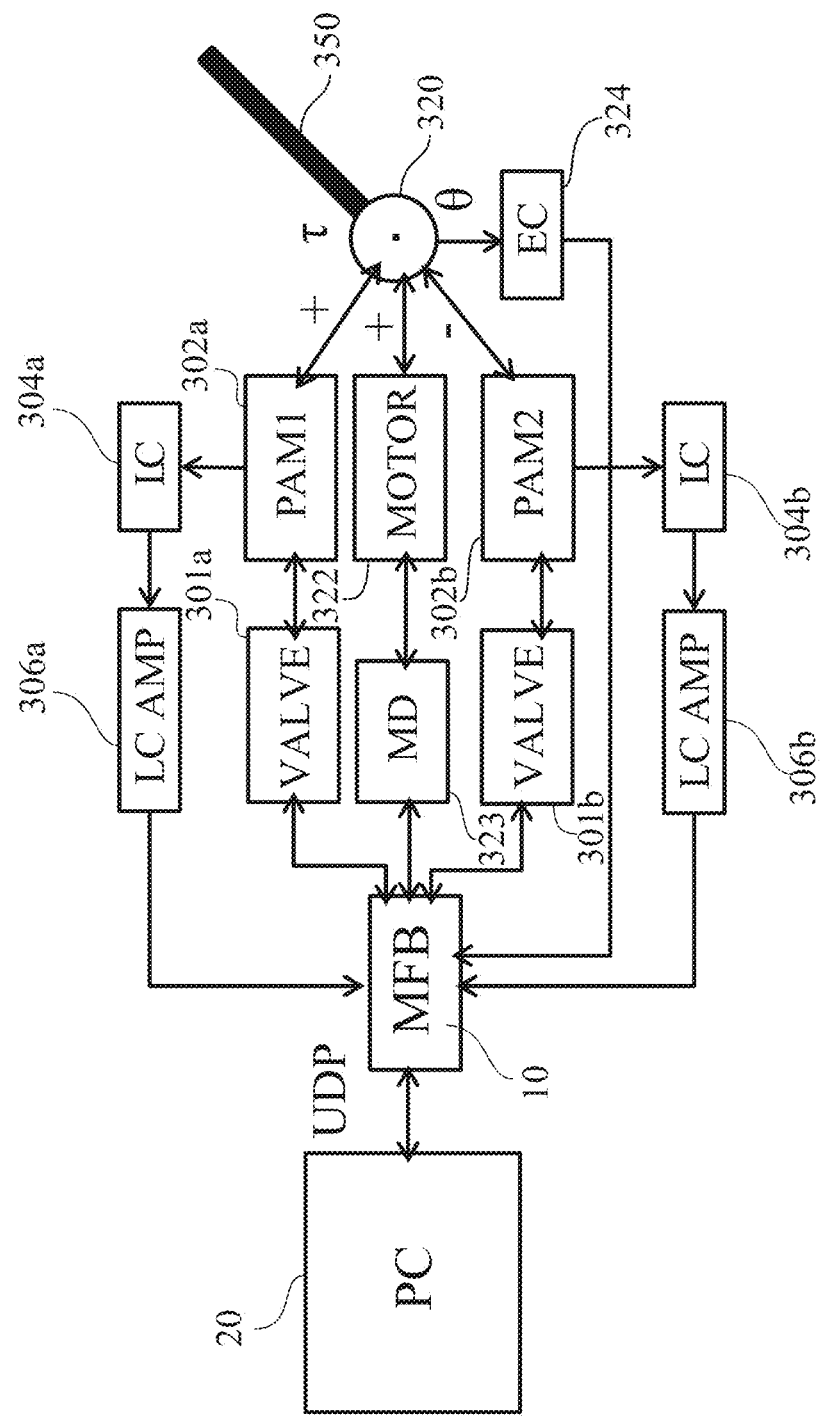
FIG. 6 is a functional block diagram showing a configuration for controlling a pneumatic-electric hybrid actuator system operating with one degree of freedom.

FIG. 6 is a functional block diagram showing a configuration for controlling a pneumatic-electric hybrid actuator system operating with one degree of freedom shown in FIG. 3.

In FIG. 6, internal control device 10 is formed as a multi function board.

A multi function board 10 connected to external control device 20 controls the actuator in accordance with a command from external control device 20. Specifically, multi function board 10 controls valves 301a and 301b for controlling contraction of pneumatic air muscles 302a and 302b, and a motor driver 323 for controlling electric motor 322. Further, multi function board 10 reads measurement data from angle encoder 324 detecting the joint angle θ, from load cells 304a and 304b detecting driving forces from air muscles, and from the torque sensor detecting torque exerted on active joints, and based on the read data, controls the torque to be applied.

Load cell amplifiers 306a and 306b amplify outputs from load cells 304a and 304b and transmit them to multi function board 10.

Driving forces from air muscles 302a and 302b as well as from electric motor 322 are combined at rotational joint by pulley 320, and whereby torque ti is applied to arm 350.

By the hybrid type actuator having such a structure as described above, it is possible to attain both driving force and responsiveness and to reduce inertia at the movable portion.

Further, by the volume of pipe cylinder 108, the volume of introducing compressed air in the artificial muscle chamber of flexible material 100 reduces and, assuming that the same contraction force is to be generated, responsiveness of air muscle 302 also improves.

Further, when a pressure-tension converting module that does not expose any of the artificial muscle, the sensors and the movable parts can be formed, maintenance can be made easier when a plurality of such modules are mounted to a frame of the controller unit.

Second Embodiment

Figure 7:
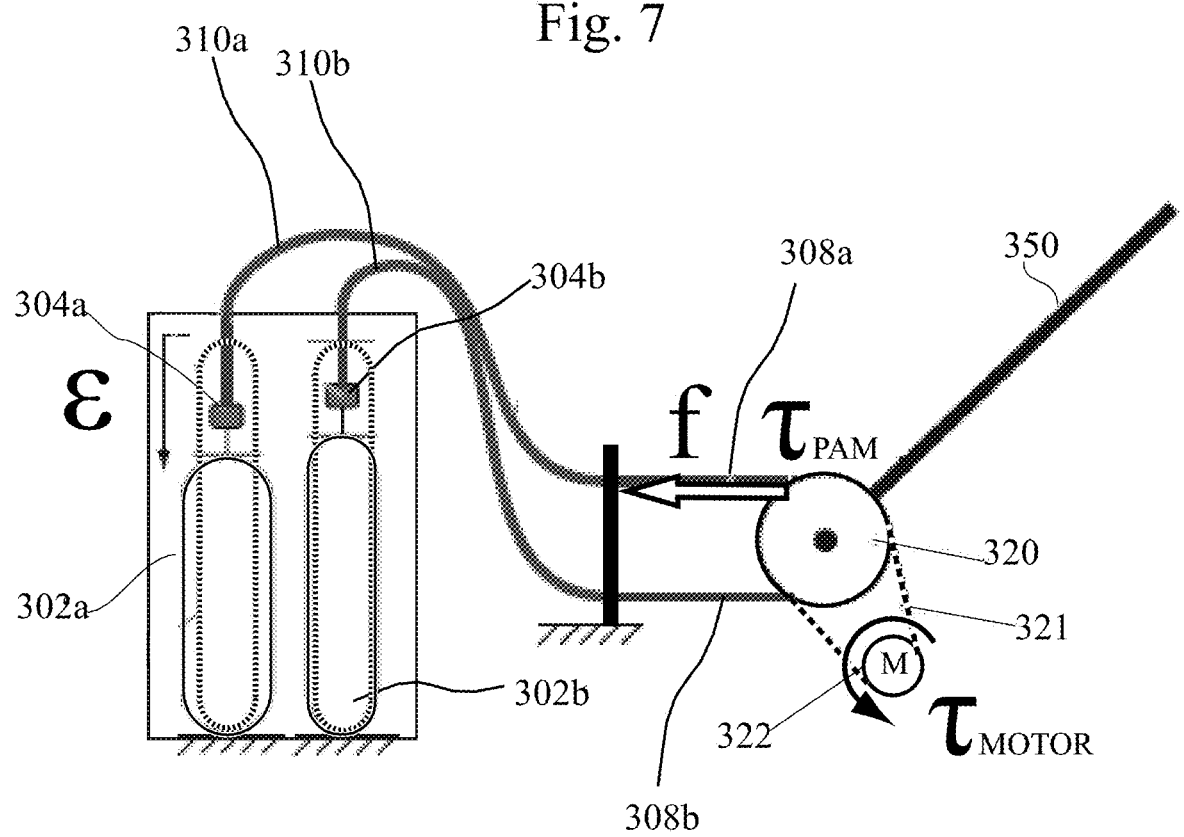
FIG. 7 shows a structure of a pneumatic-electric hybrid actuator system of one degree of freedom in accordance with Second Embodiment.

FIG. 7 shows a structure of a pneumatic-electric hybrid actuator system of one degree of freedom (PEHA 1-DOF) in accordance with Second Embodiment.

This figure corresponds to FIG. 3 of First Embodiment and the differences are as follows.

First, as will be described later, the structure of pneumatic air muscles 302$a'$ and 302$b'$ is different from First Embodiment. Further, the difference in structure of pneumatic air muscles 302$a'$ and 302$b'$ necessitates load cells 304$a$ and 304$b$ being provided on that side on which the upper end sides of pneumatic air muscles 302$a'$ and 302$b'$ are coupled with Bowden cables 310$a$ and 310$b$.

Figure 8:
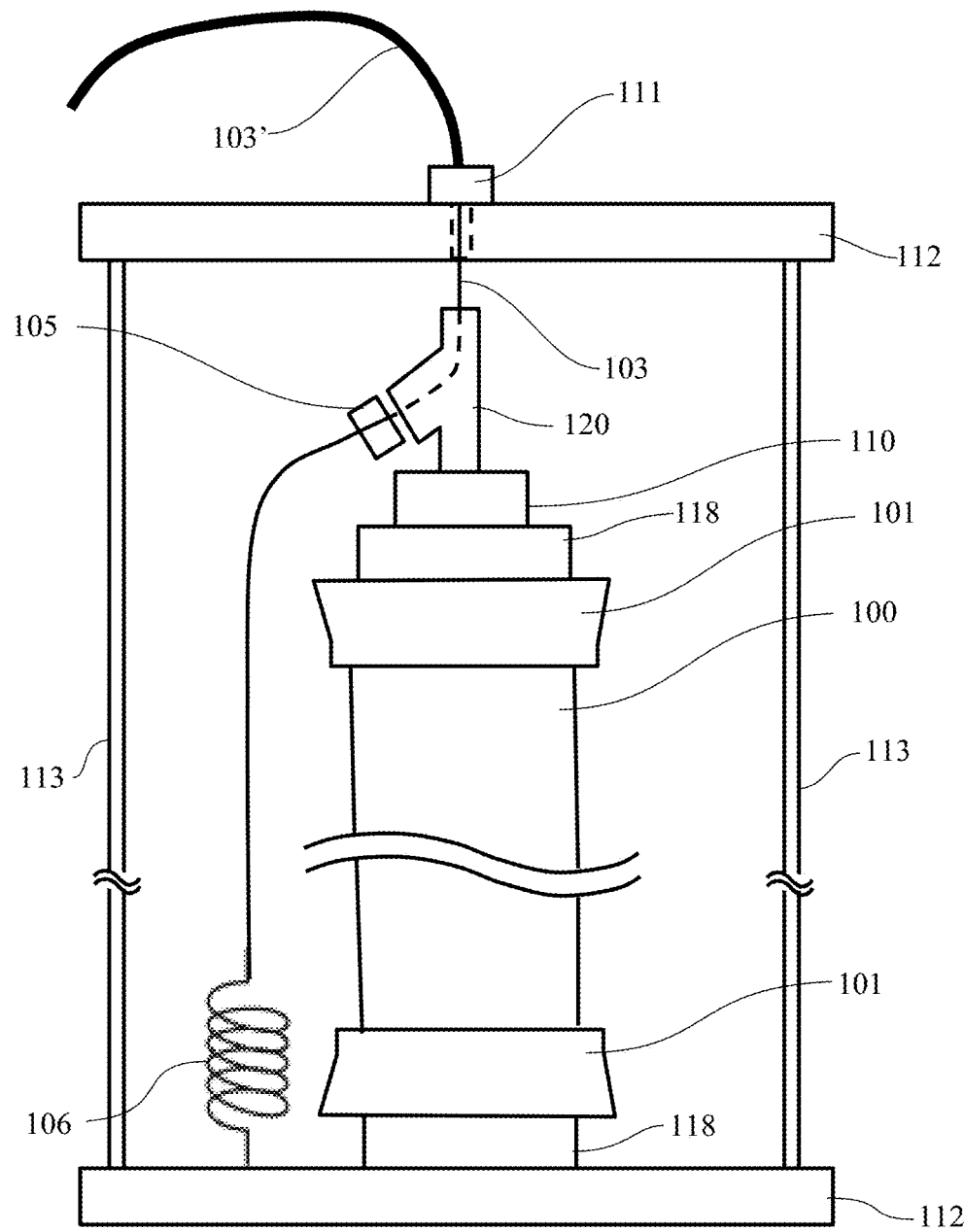
FIG. 8 is a cross-sectional view showing a structure of a pneumatic air muscle 302' in accordance with Second Embodiment.

FIG. 8 is a cross-sectional view showing a structure of a pneumatic air muscle 302' in accordance with Second Embodiment.

Since this figure corresponds to FIG. 4, mainly the differences will be described.

First, the structure of pneumatic air muscle formed of element 101 and flexible material 100 is the same as before.

The lower end of pneumatic air muscle is connected to a lower plate 112 of the frame by an element 118. An upper end of pneumatic air muscle is connected through element 118 and a load cell 110 to an element 120.

Element 20 has such a shape of a first cylinder extending in a main axial direction coupled with a second cylinder inclined obliquely downward, and a through hole allowing passage of wire 103 is provided from the center of the first cylinder to the center of the second cylinder. Inner wire 103 passes through this through hole and then connected by a resilient member (for example, a spring) 106 to the lower plate 112 of the frame.

Near the position where inner wire 103 passes through the through hole, a stopper 105 is fixed on wire 103. Stopper 105 is larger than the through hole of element 120; therefore, at a portion where the upper end of stopper 105 abuts the lower end of element 120 when the pneumatic air muscle contracts, inner wire 103 is integrated with element 120, and the contraction force of flexible material 100 is transmitted to wire 103.

Except these points, the structure is the same as that of FIG. 4; therefore, description thereof will not be repeated here.

Figure 9:
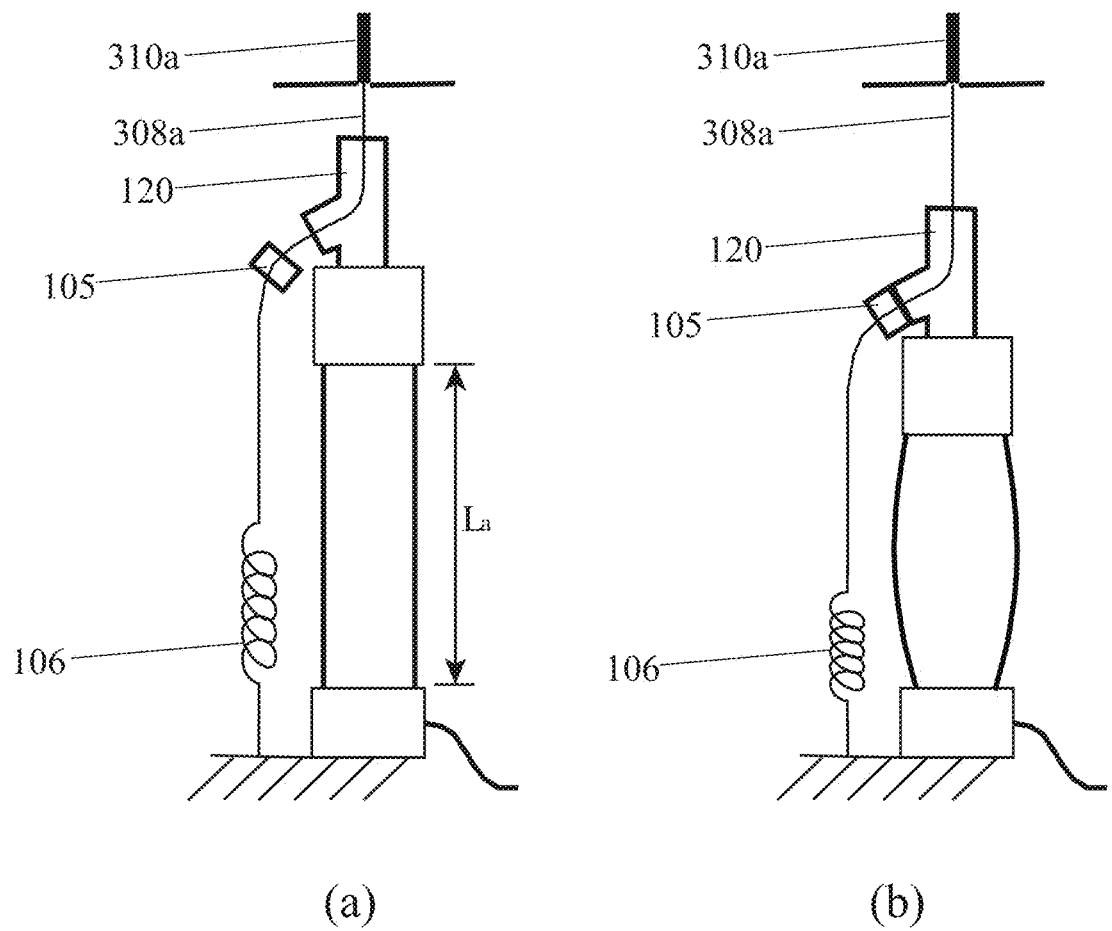
FIG. 9 schematically illustrates extended and contracted states of the pneumatic air muscle.

FIG. 9 schematically illustrates extended and contracted states of the pneumatic air muscle 302' shown in FIG. 8.

As described above, at a portion where the upper end of stopper 105 abuts the lower end of element 120 when the pneumatic air muscle 302' contracts, inner wire 103 is integrated with element 120, and the contraction force of flexible material 100 is transmitted to wire 103.

On the other hand, spring 106 is a member for pulling inner wire 103 downward and, when stopper 105 moves away from element 120, spring 106 applies certain tension to wire 103, to prevent slacking of wire 103.

Figure 10:
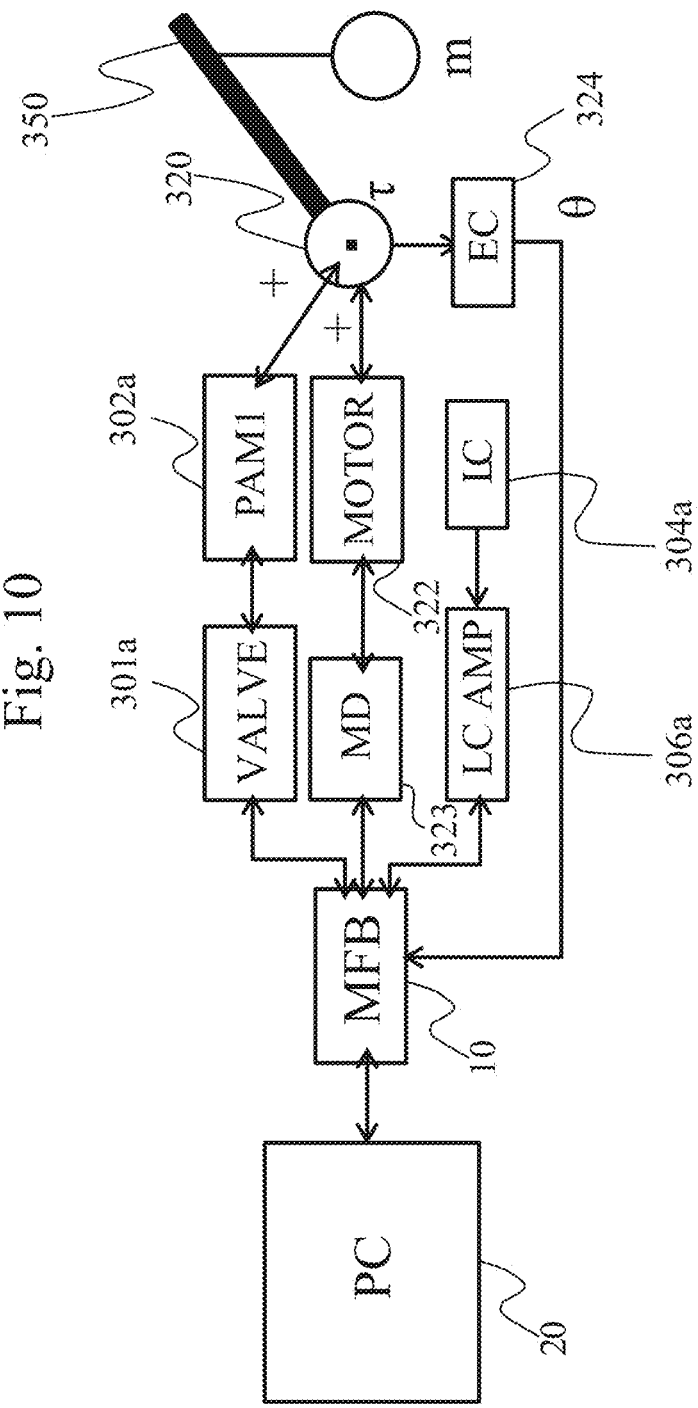
FIG. 10 is a functional block diagram showing a configuration for controlling a pneumatic-electric hybrid actuator system operating with one degree of freedom.

FIG. 10 is a functional block diagram showing a configuration for controlling a pneumatic-electric hybrid actuator system operating with one degree of freedom shown in FIG. 7.

It is noted that in this figure, a control system of only one of the pneumatic air muscle is shown.

Multi function board 10 connected to external control device 20 controls the actuator in accordance with a command from external control device 20. Specifically, multi function board 10 controls a valve 301$a$ for controlling contraction of pneumatic air muscle 302$a$ and a motor driver 323 for controlling electric motor 322. Further, multi function board 10 reads measurement data from angle encoder 324 detecting the joint angle θ, from load cell 304$a$ detecting driving force from the air muscle, and from the torque sensor detecting torque exerted on active joints, and based on the read data, controls the torque to be applied.

Load cell amplifier 306$a$ amplifies an output from load cell 304$a$ and transmits it to multi function board 10.

Driving forces from air muscle 302$a$ and from electric motor 322 are combined at rotational joint by pulley 320, and whereby torque τ is applied to arm 350.

Figure 11:
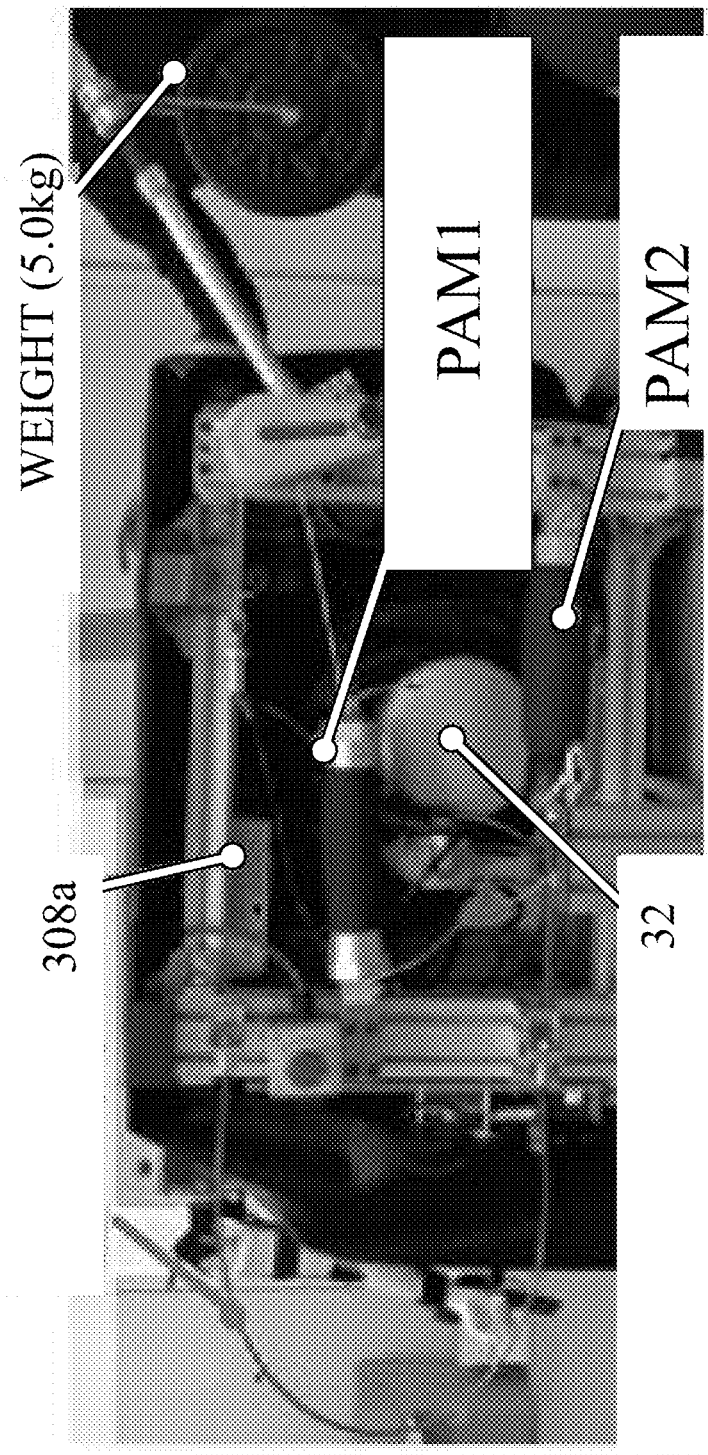
FIG. 11 shows an appearance of a prototype of pneumatic-electric hybrid actuator operating with one degree of freedom.

FIG. 11 shows an appearance of a prototype of pneumatic-electric hybrid actuator operating with one degree of freedom shown in FIG. 7.

FIG. 11 shows a 1-DOF system for testing the PEHA provided with the Bowden cable, in which a pneumatic air muscle (lower side of FIG. 11, PAM 2) is provided away from the joint system and the contraction force is transmitted through the flexible coat on the outside and through the cable inside the Bowden cable.

It is noted that the pneumatic air muscle (PAM 1) on the upper side of FIG. 11 is used to put safety limit on the magnitude of torque applied to the joint, rather than applying a contraction force.

Figure 12:
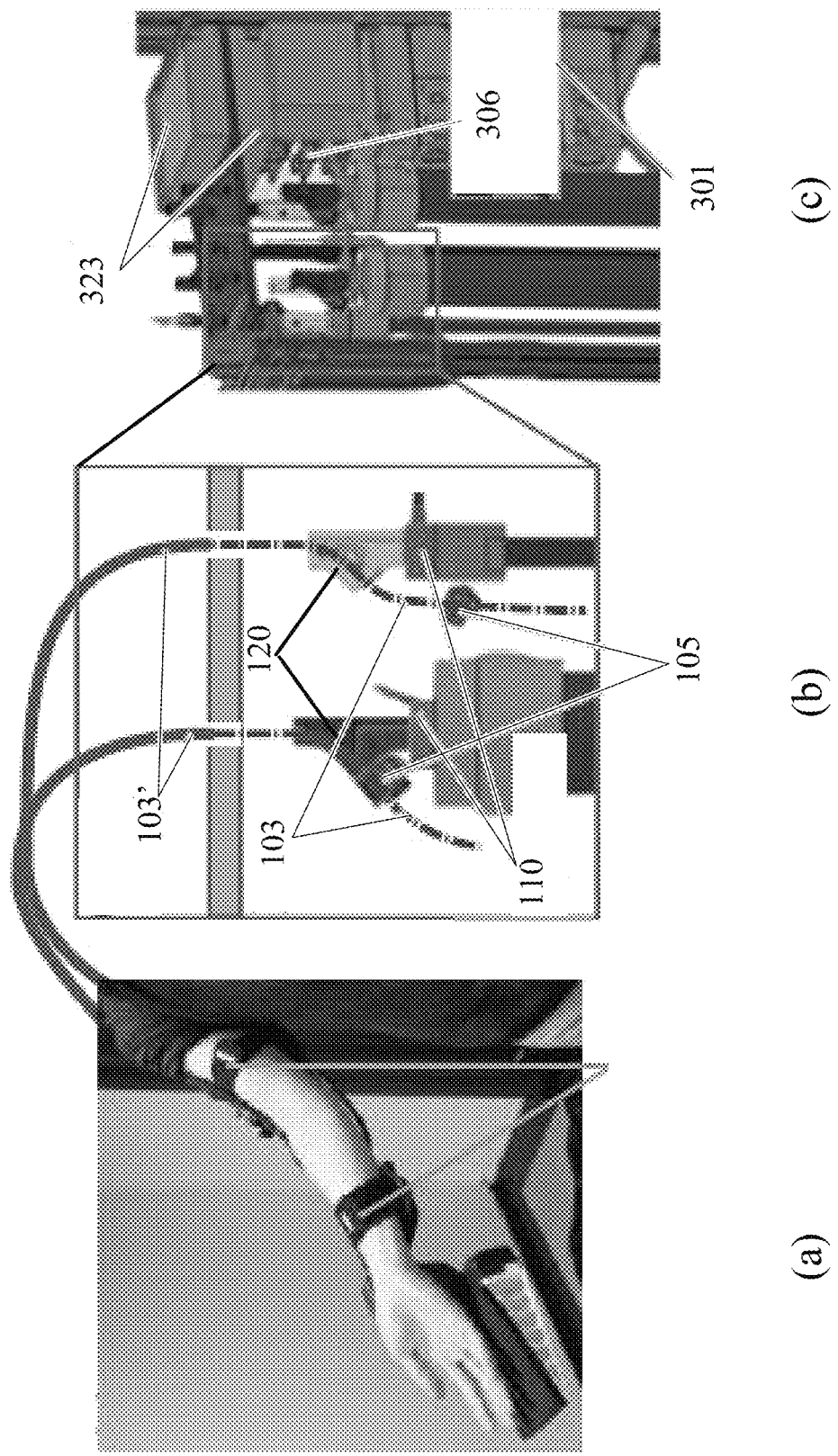
FIG. 12 shows a structure of a controller unit 1.

FIG. 12 shows a structure of a controller unit 1.

In FIG. 12, (a) shows an appearance of a right arm of a prototype and the user's arm wearing the exoskeleton arm.

To couple the exoskeleton on the user's arm, belts are provided at coupling portions between the elbow and the wrist and between the shoulder and the elbow.

FIG. 12 shows, at (b) and (c), a controller unit 1 mechanically independent from the exoskeleton arm structure and connected by a Bowden wire and an electric cable.

In FIG. 12, (b) shows a structure for preventing slacking of inner wire by the passive movement on the pulley side, as described with reference to FIG. 8.

When the shoulder angle lowers, inner wire 103 puts down itself toward the pneumatic air muscle. The side of pneumatic air muscle must be constantly controlled so that the wire does not become loose. Otherwise, the wire may be wrenched and go off from the pulley groove. Therefore, when the contraction force is to be transmitted, inner wire 103 is engaged with element 120 by stopper 105 and moves in coordination with pneumatic air muscle, and when it moves in the opposite direction, stopper 105 comes off from element 120 and the wire is pulled downward by spring 106, not shown, so that certain tension is maintained.

In FIG. 12, (c) shows alignment of the pneumatic air muscle and a valve.

Multi function board 10 and load cell amplifier 306 are also positioned below motor driver 323.

The controller unit is externally connected for an AC power source (100-240V), for an air line to the compressor, and for an Ethernet (registered trademark) cable for communication with external control device 20.

The shoulder portion of an upper limb exoskeleton is mounted on a stable frame placed on the ground, and in the frame of controller unit, an air tank 32, internal control device 10 and a power source 50 are provided in addition to the pneumatic air muscle.

For silence, only a scroll type compressor 42 is provided behind the frame outside of this structure and it feeds air pressure.

The power-to-weight ratio is very high, and the pneumatic air muscle used in the exoskeleton arm can produce force up to 5000 N.

In contrast, when such a large force is to be transmitted, the Bowden cable or wire stopper is inoperative.

Therefore, for the structure shown in FIG. 11, safety limit is ensured by preliminary tests, and the pneumatic air muscle (PAM 1) on the upper side of FIG. 11 is used for providing safety limit in the magnitude of torque applied on the joint, rather than for applying contraction force, as described above.

In FIG. 11, only the control of force of the pneumatic air muscle in the upper direction is considered. For example, it is assumed that the force to be controlled of the antagonistic muscle is constant and the joint follows this constraint.

The following points must be considered when controlling the air muscle.

First, the force of the pneumatic air muscle is caused by the ratio of contraction and is very non-linear.

This point is disclosed, for example, in the following article.

Known Literature Document 1: A. Hildebrandt, O. Sawodny, R. Neumann, and A. Hartmann, "Cascaded control concept of a robot with two degrees of freedom driven by four artificial pneumatic muscle actuators," pp. 680-685, 2005.

In addition, operation with large force causes considerable extension of the cable between the encoder and the pneumatic air muscle, possibly resulting in estimate error of the contraction ratio of the pneumatic air muscle.

Second, loss of force between the external case and the inner cable in the Bowden cable transmission system is not explicitly considered.

Friction of the Bowden cable may be corrected by extending the static friction coefficient model disclosed in the following article to a continuous model.

Known Literature Document 2: L. E. Carlson, B. D. Veatch, and D. D. Frey, "Efficiency of Prosthetic Cable and Housing," JPO: Journal of Prosthetics and Orthotics, vol. 7, no. 3, p. 96, 1995.

Further, contraction force model of the pneumatic air muscle is described as a function of second order polynominal expression at an equilibrium point, in the following two articles.

Known Literature Document 3: K. Inoue, "Rubbertuators and applications for robots," in Proceedings of the 4th international symposium on Robotics Research. MIT Press, 1988, pp. 57-63.

Known Literature Document 4: D. Caldwell, A. Razak, and M. Goodwin, "Braided pneumatic muscle actuators," in Proceedings of the IFAC Conference on Intelligent Autonomous Vehicles, 1993, pp. 507-512.

Further, for an operation with a large force, mechanical deformation and extension of the inner wire must also be considered.

This problem can be addressed by considering a tendon spring model for a pneumatic-electric hybrid system disclosed in the following article.

Known Literature Document 5: T. Noda, N. Sugimoto, J. Furukawa, M. Sato, S. Hyon, and J. Morimoto, "Brain-controlled exoskeleton robot for bmi rehabilitation," Proceedings of IEEE-RAS International Conference on Humanoids (Humanoids), 2012.

Results of experiments of actual prototype control using such a control structure as described above are as follows.

Figure 13:
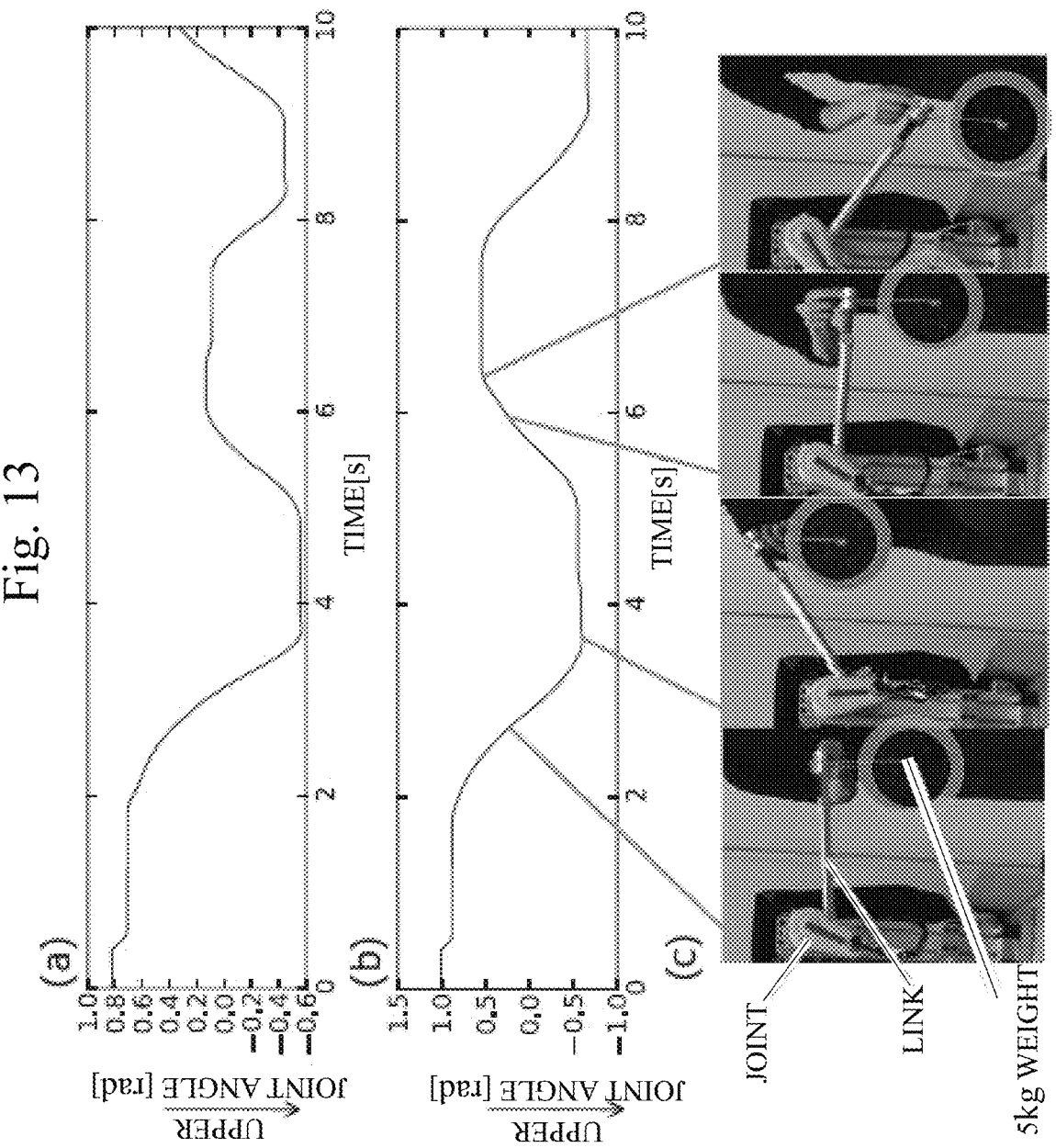
FIG. 13 shows trajectory of angles in a gravity compensating task for a system with one degree of freedom.

FIG. 13 shows trajectory of angles in a gravity compensating tasks for a system with one degree of freedom.

In FIG. 13, (a) and (b) show joint angles measured in 2.5 kg and 5.0 kg gravity compensating tasks, and (c) shows snap-photos taken during the weight compensating operation.

For gravity compensation, vertical assisting force and joint torque for the gravity are generated in accordance with the following.

$$\tau = J^T G_{r+h}$$

where J represents COM Jacobian matrix and $G_{r+h}$ represents desired virtual force, as desired torque at each joint.

If a subject moves and releases the system and the joint angle is maintained, then it is confirmed that the feed-forward torque-based controller successfully operates in the task.

Horizontal areas in the graphs (a) and (b) of FIG. 13 indicate that the weight is kept after the release.

Here, large torque is generated to maintain the weight, while the joint is back-drivable. The arm holding 5.0 kg can easily be moved upward and downward by a single finger.

By the hybrid actuator having such a structure also, it is possible to attain both driving force and responsiveness and to reduce inertia at the movable portion, like the First Embodiment.

Further, when a pressure-tension converting module that does not expose any of the artificial muscle, the sensors and the movable parts can be formed, maintenance can be made easier when a plurality of such modules are mounted to a frame of the controller unit.

The actuator device in accordance with the embodiments described above may be used not only for exoskeleton robots but also for the driving system for humanoid robots.

The embodiments as have been described here are mere examples and should not be interpreted as restrictive. The scope of the present invention is determined by each of the claims with appropriate consideration of the written description of the embodiments and embraces modifications within the meaning of, and equivalent to, the languages in the claims.

INDUSTRIAL APPLICABILITY

The present invention is applicable to power assist robots assisting movements of users and to humanoid robots.

REFERENCE SIGNS LIST 1 controller unit, 10 internal control device, 20 external control device, 40 exoskeleton robot, 100 flexible material, 105 stopper, 109 and 120 elements, 121 exoskeleton, 122 active joint, 123 passive joint, 124 detecting mechanism, 302a and 302b pneumatic air muscle, 308a and 308b inner wire, 310a and 310b Bowden cable, 320 pulley, 321 transmission mechanism, 322 electric motor

The invention claimed is:

1. An actuator device driven by fluid pressure, comprising:
 a fluid pressure artificial muscle having fixed first end, a second end opposite to the first end, the artificial muscle contracting in a longitudinal contraction direction with increase of said fluid pressure introduced from outside to a fluid bladder for driving;
 a flexible cable for transmitting contraction force of said fluid pressure artificial muscle from the second end of said fluid pressure artificial muscle to an object to be driven;
 a stopper fixed at a prescribed position on said cable;
 an engaging member provided on the second end of said fluid pressure artificial muscle for transmitting the contraction force of said fluid pressure artificial muscle to said cable by engaging with said stopper in response to contraction of said fluid pressure artificial muscle being a prescribed amount or larger; and
 a resilient tensioner applying tensile force to said cable in the longitudinal contraction direction of said fluid pressure artificial muscle to maintain tension, thus preventing slacking of the cable when the artificial muscle is not contracted, said fluid pressure artificial muscle including, a cylinder provided in said fluid pressure artificial muscle, fixed to said other end of said fluid pressure artificial muscle and having the inside sealed from said fluid pressure; wherein said engaging member is a lid of said cylinder provided at said other end of said fluid pressure artificial muscle, said lid having a through hole through which said cable passes, said stopper is fixed to said cable inside said cylinder, has an outer diameter not smaller than said through hole and is engageable with said through hole, and said resilient tensioner coupling said stopper with a bottom portion of said cylinder.

2. The actuator device according to claim 1, wherein said cable is a Bowden cable.

3. The actuator device according to claim 1, wherein
 said fluid pressure artificial muscle have second end fixed inside a frame structure; and
 said cable is coupled with said object to be driven through a through hole at one end side of said frame structure.

4. The actuator device according to claim 3, wherein a force sensor for detecting contraction force of said fluid pressure artificial muscle is provided between an inner surface of the other end side of the inside of said frame structure and said fluid pressure artificial muscle.

5. The actuator device according to claim 1, wherein
 said object to be driven is a joint structure body;
 said actuator device further comprising:
 a pulley provided at a movable portion of said joint, receiving first torque by said contraction force transmitted by said cable; and
 an electric motor coupled to said pulley, for applying second torque to said pulley.

6. The actuator device according to claim 1, further comprising a sensor for detecting contraction rate of said fluid pressure artificial muscle by measuring a distance between the outer bottom of said cylinder and the inner surface of said fixed one end of said fluid pressure artificial muscle.

7. A power assist robot assisting musculoskeletal movement of a user, comprising:
 a frame corresponding to an exoskeleton;
 an active joint arranged for applying a support force to a joint of said user as an object in said musculoskeletal movement; and
 an actuator device according to claim 1, the actuator device driving said active joint; and
 a control unit for operating said active joint by controlling torque to said active joint.

8. A humanoid robot, comprising:
 a frame structure corresponding to a human skeleton;
 an active joint arranged to apply a driving force to a joint of said frame structure; and
 an actuator device according to claim 1, the actuator device driving said active joint.

* * * * *